(12) United States Patent
Morris et al.

(10) Patent No.: US 9,370,433 B1
(45) Date of Patent: Jun. 21, 2016

(54) EXPANDABLE FUSION DEVICE AND METHOD OF USE THEREOF

(71) Applicant: Alliance Partners, LLC, San Antonio, TX (US)

(72) Inventors: Frankie Morris, Austin, TX (US); Justin Rice, San Antonio, TX (US); Mike Faraj, San Antonio, TX (US); Jeff Smith, Cibolo, TX (US)

(73) Assignee: Alliance Partners, LLC, San Antonio, TX (US)

( * ) Notice: Subject to any disclaimer, the term of this patent is extended or adjusted under 35 U.S.C. 154(b) by 0 days.

(21) Appl. No.: 14/673,250

(22) Filed: Mar. 30, 2015

(51) Int. Cl.
*A61F 2/44* (2006.01)

(52) U.S. Cl.
CPC ............... *A61F 2/4455* (2013.01); *A61F 2/442* (2013.01); *A61F 2250/0009* (2013.01)

(58) Field of Classification Search
CPC .................. A61F 2/4455; A61F 2/447; A61F 2002/30556; A61F 2002/30484; A61F 2002/3037; A61F 2002/30398; A61F 2002/304; A61F 2002/30401; A61F 2002/30518; A61F 2002/3052; A61F 2002/4625; A61F 2/44; A61F 2/4611
See application file for complete search history.

(56) References Cited

U.S. PATENT DOCUMENTS

| | | | |
|---|---|---|---|
| 2013/0023994 A1* | 1/2013 | Glerum | A61F 2/447 623/17.16 |
| 2014/0094916 A1* | 4/2014 | Glerum et al. | 623/17.15 |

* cited by examiner

*Primary Examiner* — Samuel Hanna
(74) *Attorney, Agent, or Firm* — Greenberg Traurig, LLP; Ross Spencer Garsson

(57) ABSTRACT

An expandable fusion device capable of being inserted between adjacent vertebrae and expanded laterally to facilitate the fusion process and the use of such device. The expandable fusion device can expand laterally such that it expands the cross-sectional support area of the device to provide more stable support of the support the spine and maintain the normal spacing between opposing vertebrae. The interior area of the expandable fusion device (in which the bone graft can be packed) does not decrease (and generally increases) during expansion of the device. This facilitates pre-packing of the expandable fusion device before utilization.

8 Claims, 24 Drawing Sheets

1003a
1003b

US 9,370,433 B1

EXPANDABLE FUSION DEVICE AND METHOD OF USE THEREOF

FIELD OF INVENTION

An expandable fusion device for promoting an intervertebral fusion, and more particularly, an expandable fusion device capable of being inserted between adjacent vertebrae and expanded laterally to facilitate the fusion process.

BACKGROUND OF INVENTION

The spine is the axis of the skeleton on which all of the body parts hang. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation and translation.

Typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

The success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth.

Cages have been developed to help support the spine and maintain the normal spacing between opposing vertebrae. Typically, cages are pre-manufactured at various heights requiring that a cavity between opposing vertebrae be prepared and distracted to a dimension corresponding to the most suitably sized cage. The surgical procedure to prepare the implant site can be difficult and lengthy. Moreover, the procedure can increase risk of trauma to the tissues surrounding of the implant site.

Distractible cages may be used as both a fusion device and/or a means for maintaining intervertebral spacing. Often these implants include a drive means that allows the cage to be expanded in situ to a size that corresponds to the cavity created when the damaged tissue is removed. The drive means typically includes devices such as gears, threaded rods, and the like, in mechanical engagement so as to expand or contract the device to a necessary distance between the vertebrae.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances (i.e., bone graft). These devices are implanted between adjacent vertebral bodies in order to fuse the vertebral bodies together, alleviating the associated pain. Examples of such fusion devices are taught and described the following U.S. Pat. Nos. 6,830,589, 8,062,375, 8,435,298, 8,518,087, and 8,556,979 and the There are drawbacks associated with the known conventional fusion devices and methodologies. For example, while current expandable cages are designed to expand in height, their lateral profile remains the same (or is decreased) as they are expanded. Accordingly, there is a need for expandable fusion devices that expand laterally and a further need for expandable fusion devices that can expand laterally.

Moreover, it is advantageous to pack cages with bone graft. In view of the gears, threaded rods, and the like various used to expand the cages, packing such bone graft is more difficult. Accordingly, there is a need for an improved expandable fusion device that has the open volume for the bone graft and openings (i.e., graft windows) that render this open volume readily accessible.

SUMMARY OF INVENTION

The present invention is an expandable fusion device capable of being inserted between adjacent vertebrae and expanded laterally to facilitate the fusion process. In some embodiments of the present invention, the expandable fusion device expands laterally. The expandable fusion device can expand laterally such that it expands the cross-sectional support area of the device to provide more stable support of the support the spine and maintain the normal spacing between opposing vertebrae. The interior area of the expandable fusion device (in which the bone graft can be packed) does not decrease (and generally increases) during expansion of the device. This facilitates pre-packing of the expandable fusion device before utilization.

In general, in one aspect, the invention features an expandable fusion device that includes a main body. The main body has having an axis that runs from the back to the front of the main body, a left side, an a right side. The expandable fusion device further includes a left lateral expandable body connected to the main body and capable of moving outwardly from the left side of the main body while the left lateral expandable body remains parallel to the axis of the main body. The expandable fusion device further includes a right lateral expanding body connected to the main body and capable of moving outwardly from the right side of the main body while the left lateral expandable body remains parallel to the axis of the main body. The expandable fusion device further includes a guide body that is operable for moving within the main body along the main axis in which (i) the movement of the guide body in a first direction moves the left lateral expandable body and the right expandable body outward relative to the main body, and (ii) the movement of the guide body in a second direction (which is opposite to the first direction) moves the left lateral expandable body and the right expandable body inward relative to the main body. The expandable fusion device has an interior space formed from the main body, left lateral expanding body, and the right lateral expanding body. The interior space is adapted to be packed with bone growth inducing substances.

Implementations of the invention can include one or more of the following features:

The expandable fusion device can expand and contract without changing the height of the expandable fusion device.

The interior space of the expandable fusion device can be unreduced as the guide body is moved in the first direction.

The expandable fusion device has a width that can be increased between 1 mm and 6 mm as the guide body is moved in the first direction.

The expandable fusion device has a width that can be increased between 10% and 60% as the guide body is moved in the first direction.

The expandable fusion device can have a lateral length that does not change as the guide body is moved in the first direction and the second direction.

The lateral length can be between 22 mm and 28 mm.

The expandable fusion device can have a height that does not change as the guide body is moved in the first direction and the second direction.

The height can be between 8 mm and 14 mm.

The left lateral expandable body can be movably connected to the main body using a first left guide pin and a second left guide pin. The right lateral expandable body can be moveable connected to the main body using a first right guide pin and a second right guide pin.

The first left guide pin and second left guide pin can be attached to the left lateral expandable body. The main body can have a left horizontal channel and can be operable to permit the first left guide pin to move within the left horizontal channel in a horizontal direction that is perpendicular to the axis of the main body. The guide body can have a left diagonal channel and can be operable to permit the second left guide pin to move within the left diagonal channel in a diagonal direction such that the left lateral expandable body moves outward and inward as the guide body is moved along the axis of the main body. The first right guide pin and the second right guide pin can be attached to the right lateral expandable body. The main body can have a right horizontal channel and can be operable to permit the first right guide pin to move within the right horizontal channel in the horizontal direction. The guide body can have a right diagonal channel and can be operable to permit the second right guide pin to move within the right diagonal channel in a diagonal direction such that the right lateral expandable body moves outward and inward as the guide body is moved along the axis of the main body.

The expandable fusion device can further include a translation body that is movably connected to the guide body. The rotation of the translation body can be capable of moving the guide body along the axis of the main body.

The rotation of the translation body in one rotational direction can be capable of moving the guide body in the first direction. The rotation of the translation body in an opposition rotational direction that is opposite the one rotation direction can be capable of moving the guide body in the second direction.

In general, in another aspect, the invention features a method of using an expandable fusion device. The method includes creating disc access to a position in the disc space at which the expandable fusion device will be utilized. The method further includes preparing the disc space for receiving the expandable fusion device at the position. The method further includes inserting the expandable fusion device in the disc space. The method further includes expanding the expandable fusion device such that the width of the expandable fusion device increases by at least 10%. The method further includes verifying the expandable fusion device is positioned at the position.

Implementations of the invention can include one or more of the following features:

The expandable fusion device can include a main body. The main body can have an axis that runs from the back to the front of the main body, a left side, and a right side. The expandable fusion device can further include a left lateral expandable body connected to the main body and can be capable of moving outwardly from the left side of the main body while the left lateral expandable body remains parallel to the axis of the main body. The expandable fusion device can further include a right lateral expanding body connected to the main body and can be capable of moving outwardly from the right side of the main body while the left lateral expandable body remains parallel to the axis of the main body. The expandable fusion device can further include a guide body that can be operable for moving within the main body along the main axis in which (i) the movement of the guide body can be in a first direction that moves the left lateral expandable body and the right expandable body outward relative to the main body, and (ii) the movement of the guide body can be in a second direction (that is opposite to the first direction) that moves the left lateral expandable body and the right expandable body inward relative to the main body. The expandable fusion device can have an interior space formed from the main body, left lateral expanding body, and the right lateral expanding body. The interior space can be adapted to be packed with bone growth inducing substances.

The expandable fusion device can expand without changing the height of the expandable fusion device.

The interior space of the expandable fusion device can be unreduced during the step of expanding.

The expandable fusion device can have a width that increases between 1 mm and 6 mm during the step of expanding.

The expandable fusion device can have a width that increases between 10% and 60% during the step of expanding.

The expandable fusion device can have a lateral length that does not change during the step of expanding.

The lateral length can be between 22 mm and 28 mm.

The expandable fusion device can have a height that does not change during the step of expanding.

The height can be between 8 mm and 14 mm.

The left lateral expandable body can be movably connected to the main body using a first left guide pin and a second left guide pin. The right lateral expandable body can be moveable connected to the main body using a first right guide pin and a second right guide pin.

The first left guide pin and second left guide pin can be attached to the left lateral expandable body. The main body can have a left horizontal channel and the first left guide pin can move within the left horizontal channel in a horizontal direction that is perpendicular to the axis of the main body during the step of expanding. The guide body can have a left diagonal channel and the second left guide pin can move within the left diagonal channel in a diagonal direction such that the left lateral expandable body can move outward as the guide body is moved along the axis of the main body during the step of expanding. The first right guide pin and the second right guide pin can be attached to the right lateral expandable body. The main body can have a right horizontal channel and the first right guide pin can move within the right horizontal channel in the horizontal direction. The guide body can have a right diagonal channel and the second right guide pin can move within the right diagonal channel in a diagonal direction such that the right lateral expandable body moves outward as the guide body is moved along the axis of the main body.

The expandable fusion device can further include a translation body that can be movably connected to the guide body. The step of expanding can include rotating the translation body to move the guide body along the axis of the main body.

The rotation of the translation body in one rotational direction can move the guide body in the first direction. The rotation of the translation body in an opposition rotational direction (that is opposite the one rotation direction) can move the guide body in the second direction.

The step of expanding can include rotating the translation body with an instrument coupled to the translation body.

The method can further include packing the expandable fusion device with bone growth inducing substances before the step of inserting.

The method can further include removing the expandable fusion device from the position after healing has occurred.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

It is also to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

The present invention is an expandable fusion device for promoting an intervertebral fusion and the method of using such a device. The expandable fusion device is capable of being inserted between adjacent vertebrae and expanded laterally to facilitate the fusion process.

Expandable Fusion Device

Figure 1A:
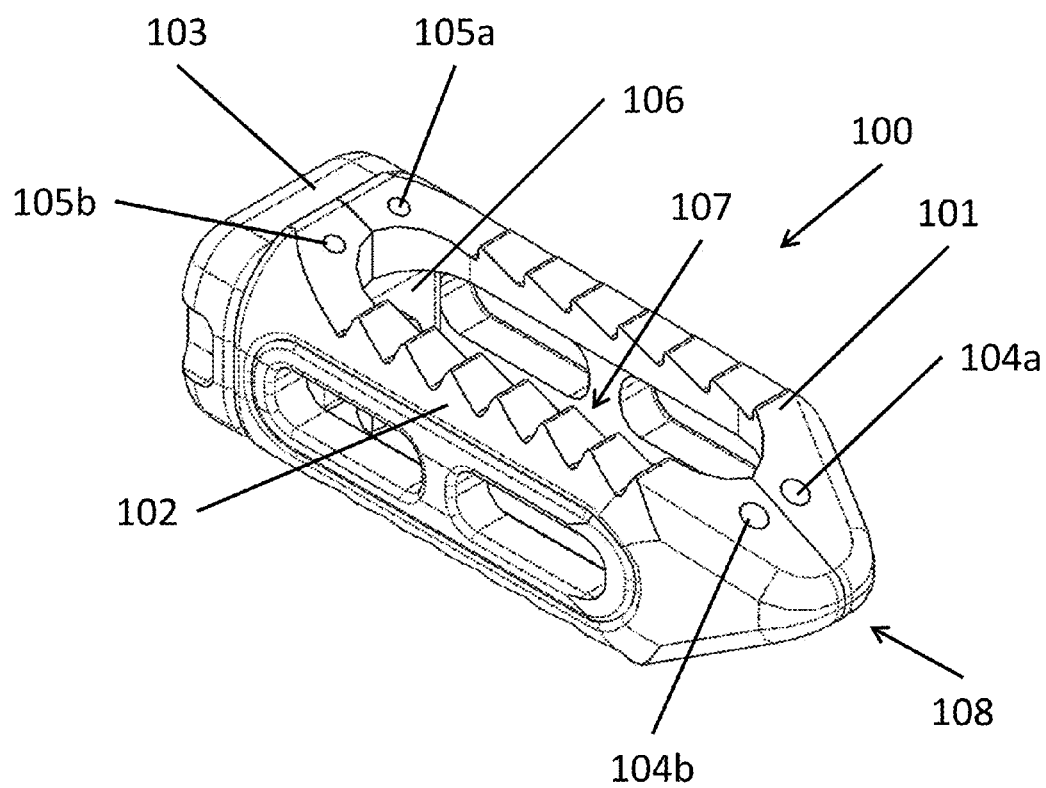
FIG. 1A is a perspective view of an embodiment of the present invention showing an expandable fusion device in a closed (fully contracted) position.
Figure 3:
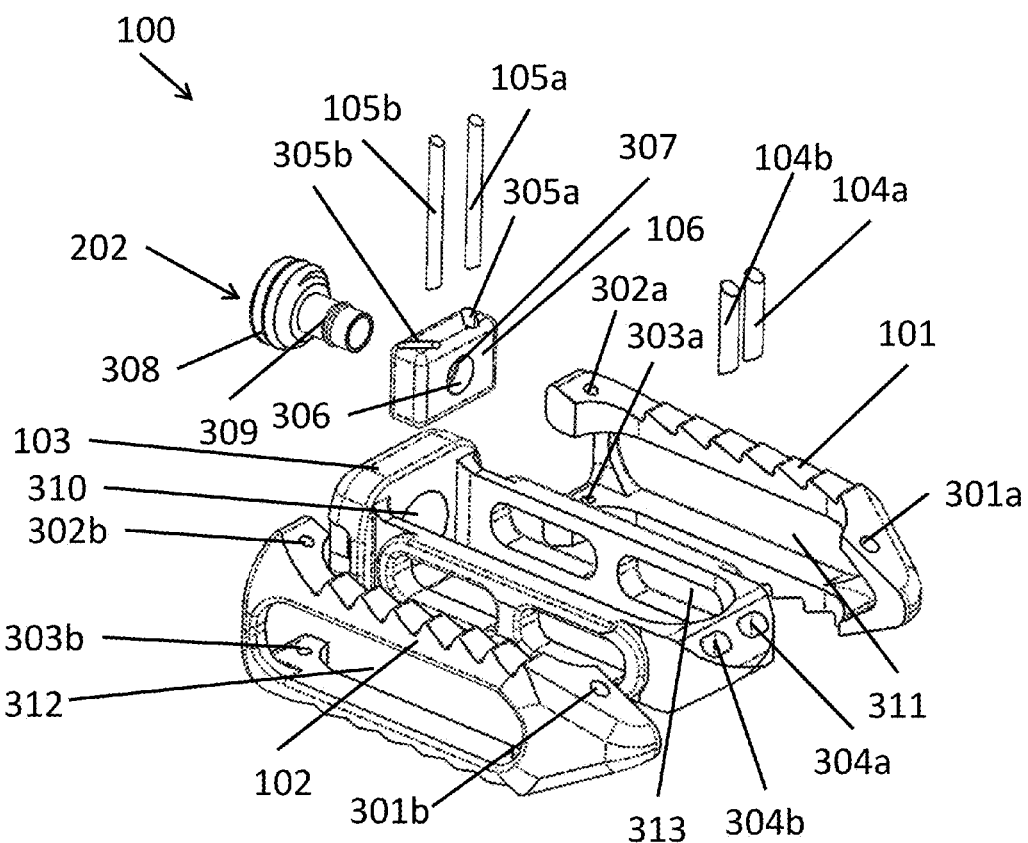
FIG. 3 is an exploded view of the embodiment of FIG. 1A.

Referring to the figures, FIG. 1A is a perspective view of an expandable fusion device 100 in a closed (fully contracted) position. (An exploded view of expandable fusion device 100 is shown in FIG. 3). Expandable fusion device 100 has a left lateral expandable body 101, a right lateral expandable body 102, and a main body 103. The front section 108 of expandable fusion device 100 is a tapered nose that aides in the insertion of the expandable fusion device 100. Above the tapered nose can be seen the tops of guide pins 104a and 104b. As shown in later figures, guide pins 104a and 104b are in horizontal guide channels 304a and 304b of main body 103 (shown in FIG. 3). Toward the back section of the expandable fusion device can be seen the tops of guide pins 105a and 105b. Guide body 106 is shown in the back section also. As shown in later figures, the guide pins 105a and 105b are in diagonal guide channels 305a and 305b of guide body 106 (shown in FIG. 3). Interior space 107 is formed by the left lateral expandable body 101, a right lateral expandable body 102, and a main body 103. Such void space 107 is accessible for packing bone graft.

Figure 1B:
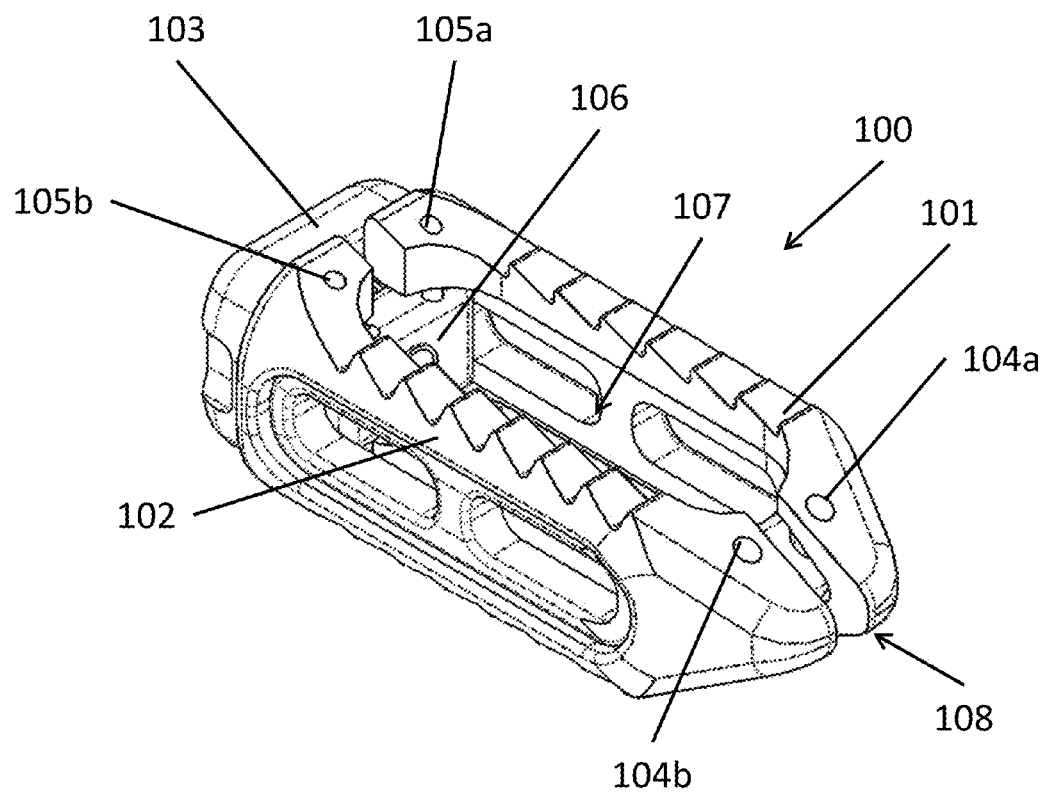
FIG. 1B is a perspective view of the embodiment of FIG. 1A in an open (fully expanded) position.

FIG. 1B is a perspective view of expandable fusion device 100 in an open (fully expanded) position. As the guide body 106 moves forward relative to expandable fusion device 100, guide pins 105a and 105b are in diagonal guide channels 305a and 305b of guide body 106 thereby causing the left lateral expandable body 101 to move outward to the left and right lateral expandable body 102 to move outward to the right relative to main body 103. Left lateral expandable body 101 and right lateral expandable body 102 remains parallel to main body parallel because guide pins 104a and 104b in the front ends of left lateral expandable body 101 and right lateral expandable body 102, can move horizontally outward in guide channels 304a and 304b of main body 103. Accordingly, as guide body 106 moves forward (relative to main body 103) the expandable fusion device expands, and as guide body 106 moves backwards (relative to main body 103) the expandable fusion device contracts. In alternative embodiments, guide body 106 is designed to move backward (relative to main body 103) to expand expandable fusion device 100, and is designed to move forward (relative to main body 103) to contract expandable fusion device 100.

Accordingly, the expandable fusion device 100 can be positioned anywhere between fully closed and fully opened.

This permits the expandable fusion device 100 to be expanded by the practitioner based upon the needs of the patient. Typically, the expandable fusion device 100 can vary between 1 mm and 6 mm from its fully closed and fully open positions. In some embodiments, the expandable fusion device can increase in its width by between 10% and 60%.

The lateral length of the expandable fusion device 100 does not change with the expanded movement of the expandable fusion device 100. Typically, the lateral length is between 22 mm and 28 mm. However, any lateral length can be utilized in the present invention.

The height of the expandable fusion device 100 also does not change with the expanded movement of the expandable fusion device 100. Typically, the height is between 8 mm and 14 mm. However, any height can be utilized in the present invention. The lateral length and height utilized will often depend on the patient to which the expandable fusion device 100 is being utilized. The height is measured as the greatest distance from the top side to the bottom side (perpendicular to the length and width). For some embodiments of extendable fusion devices, the height is generally consistent (not including the teeth, such as teeth 201 shown in FIG. 2C), i.e., the top and bottom are generally parallel to one another. This is referred to as parallel orientation and also referred to as in 0°. FIG. 2C shows an expandable fusion device in 0° (parallel orientation). In other embodiments of extendable fusion devices, the height generally decreases from front to back (not including the teeth). For instance, the expandable fusion device can have a slant of 7° (which is referred to as a lordotic orientation). The slant of the expandable fusion device is selected to correspond with lordosis tilt angle for the position at which the expandable fusion device is to be used.

Figure 2A:
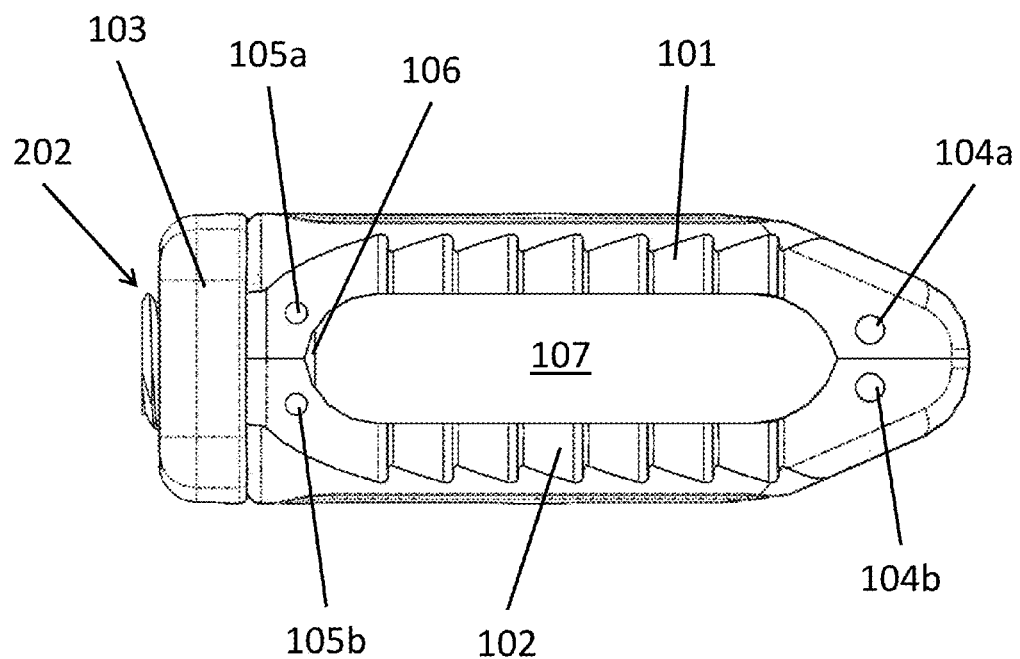
FIG. 2A is top view of the embodiment of FIG. 1A (in the closed position).
Figure 2B:
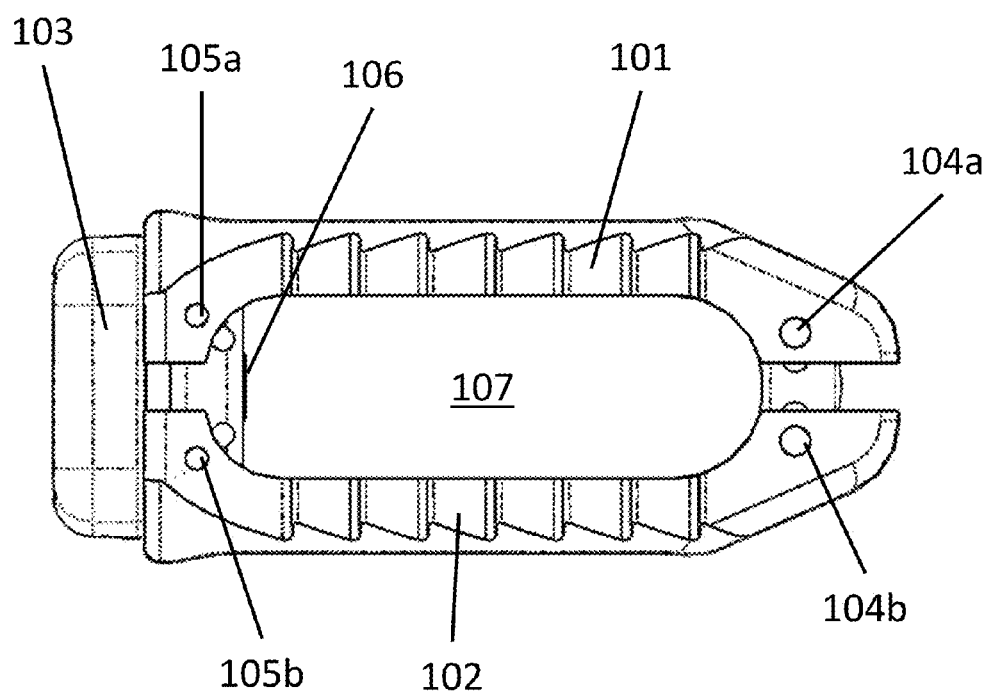
FIG. 2B is a top view of the embodiment of FIG. 1B (in the open position).
Figure 2C:
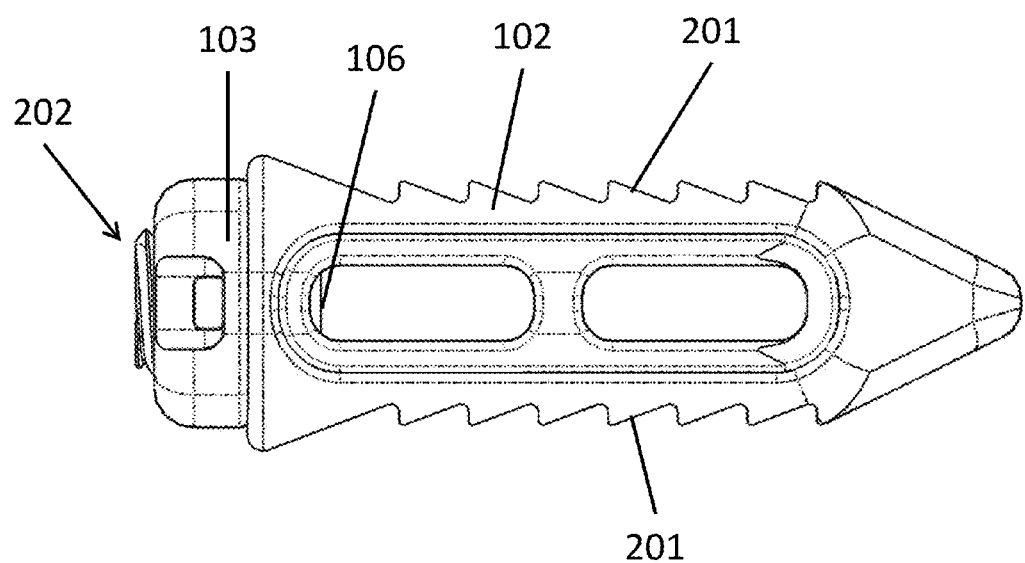
FIG. 2C is a right side lateral view of the embodiment of FIG. 1A.

FIG. 2A-2B are top views of expandable fusion device 100 (in the closed and open positions, respectively). Translation body 202 is shown at the back portion of the expandable fusion device 100, which can be rotated to move guide body 106 forward and back. As shown in more detail in FIG. 3, translation body 202 has threads that couple the inside threads in hole 310 of main body 103. As translation body 202 rotates, this moves section 309 along the axis of the main body 103. Section 309 is coupled to guide block 106 via connector 307. This allows section 109 to spin within guide block 106 and also moves guide block 106 back and forth relative to the movement of section 109 along the axis of main body 103. Accordingly, by rotating translation body 202, guide block 106 can move forward and backward relative to the axis of main body 103. Again, by such movement of the guide block 106, this moves the left lateral expandable body 101 and right lateral expandable body 102 simultaneously outward (or inward) relative to main body 103.

FIG. 2C is a right side lateral view of expandable fusion device 100. As shown in this figure, right side expandable body 102 has teeth 201 that aggressively secure fixation of the device 100 when used. Left side expandable body 101 also has teeth 201.

Figure 5A:
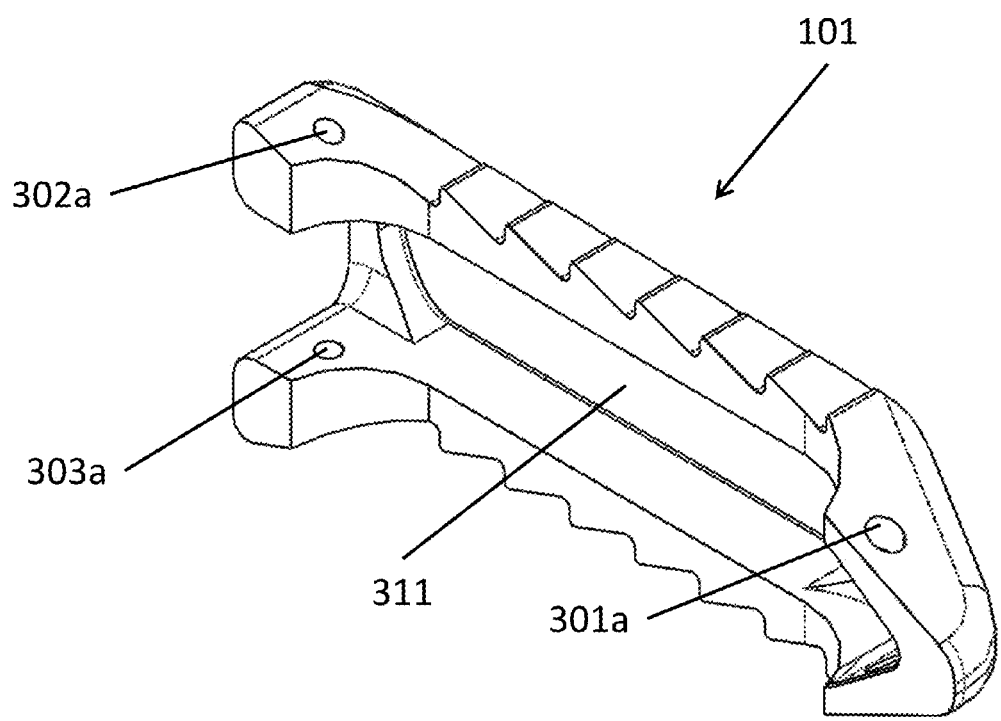
FIG. 5A is a perspective view of the left lateral expandable body of the embodiment of FIG. 1A.
Figure 5B:
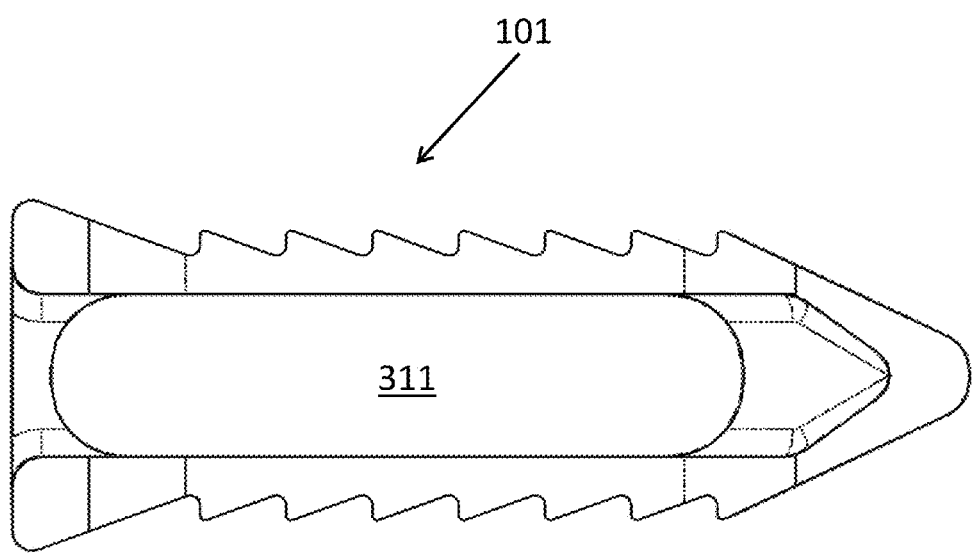
FIG. 5B is a side view of the left lateral expandable body of the embodiment of FIG. 1A.
Figure 5C:
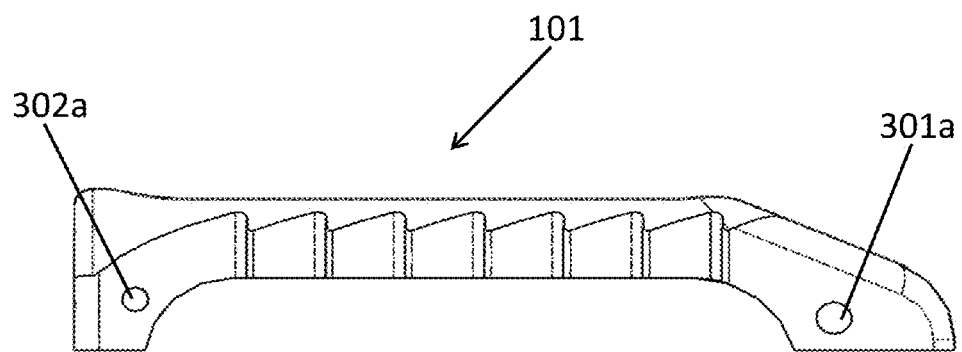
FIG. 5C is a top view of the left lateral expandable body of the embodiment of FIG. 1A.
Figure 5D:
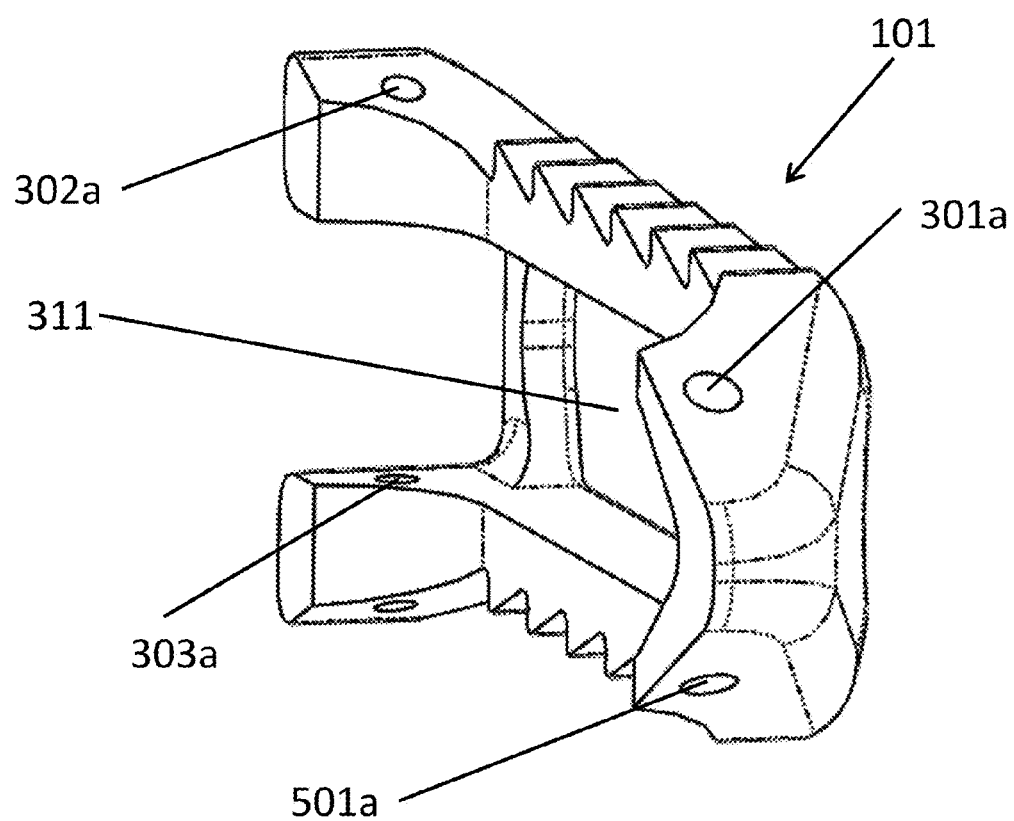
FIG. 5D is a different perspective view of the left lateral expandable body of the embodiment of FIG. 1A.
Figure 5E:
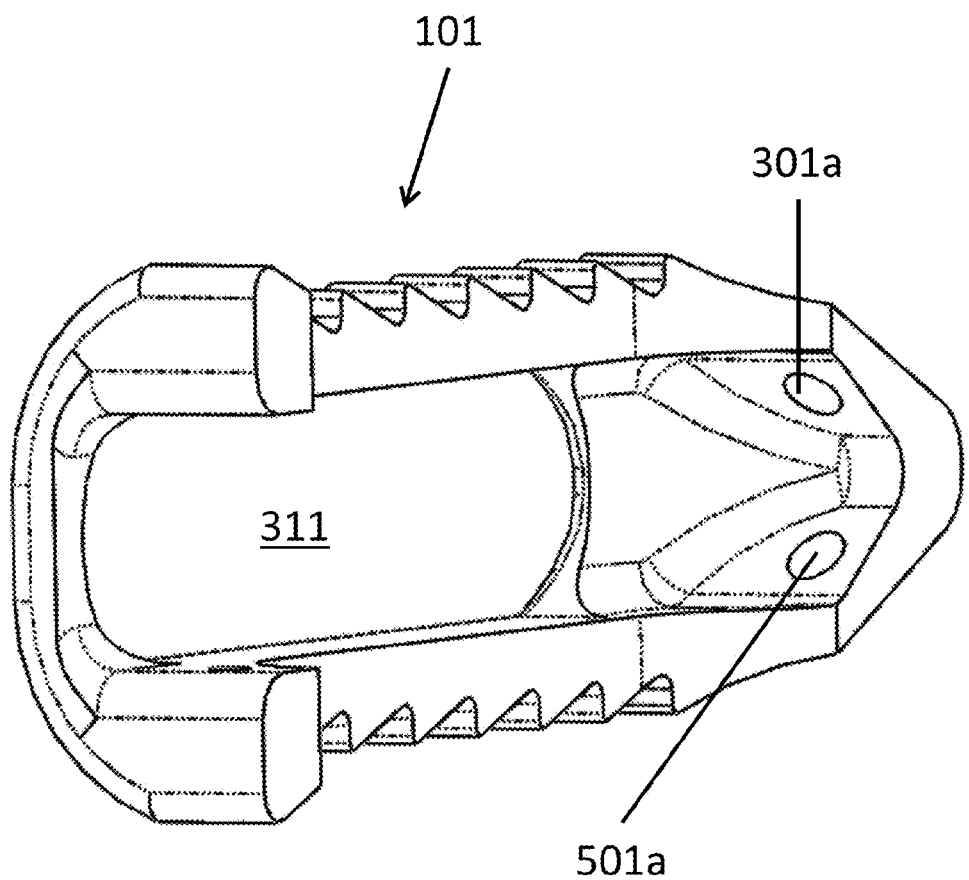
FIG. 5E is a third perspective view of the left lateral expandable body of the embodiment of FIG. 1A (which unlike the perspective views of FIG. 5A and FIG. 5D is from the back side of the left lateral expandable body.

FIG. 3 is an exploded view of expandable fusion device 100, which more clearly shows the various components of device 100. These components include:

Left lateral expanding body 101.
Right lateral expanding body 102.
Main body 103.
Guide Pins 104a and 104b.
Guide Pins 105a and 105b.
Guide body 106.
Translation body 202.
Top guide pin holes 301a and 301b (which are used for guide pins 104a and 104b, respectively). While not shown in this figure, there is a corresponding bottom pin holes that are also used for guide pins 104a and 104b, respectively. See, e.g., bottom pin hole 501a in FIG. 5D.

Top guide pin holes 302a and 302b (which are used for guide pins 105a and 105b, respectively).
Bottom guide pin holes 303a and 303b (which are used for guide pins 105a and 105b, respectively).
Horizontal guide channels 304a and 304b (which are used for guide pins 104a and 104b, respectively).
Diagonal guide channels 305a and 305b (which are used for guide pins 105a and 105b, respectively).
Hole 306 (in guide body 106).
Connector 307 (positioned in interior of hole 306).
Rotational coupler 308 (of translation body 202).
Section 309 (of translation body 202).
Hole 310 of main body 103.
Graft window 311 of left lateral expanding body 101.
Graft window 312 of right lateral expanding body 102.
Graft windows 313 of main body 103.

Figure 4:
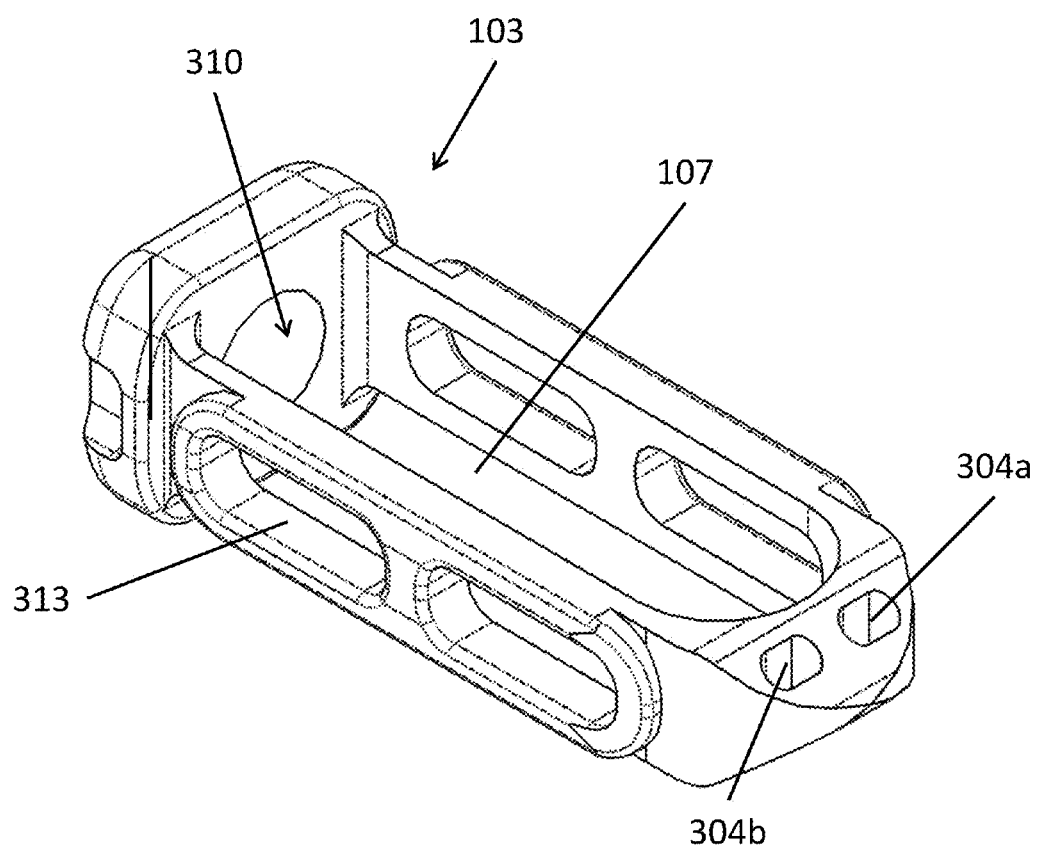
FIG. 4 is a perspective view of the main body of the embodiment of FIG. 1A.

FIG. 4 is a perspective view of main body 103. This illustrates the interior space 107 and shows how it is open at the top, bottom, and also at graft windows 313. This allows the bone graft (the grafting materials) to be packed with the interior space 107 and be open and exposed to the vertebrae during the healing process. FIG. 4 also shows the horizontal guide channels 304a and 304b in which guide pins 104a and 104b, respectively, can move horizontally (as the left lateral expanding body 101 and right lateral expanding body 102 move horizontally inward and outward relative to main body 103). FIG. 4 also shows hole 310 of main body 103 in which translation body 202 rotates about to move guide body 106 along the axis of main body 103.

FIGS. 5A-5E are various views of left lateral expandable body 101 of expandable fusion device 100. Such views are, respectively, a perspective view, a side view, a top view, another perspective view (more from the top), and a third perspective view. Such views show top guide pin hole 301a and the corresponding bottom guide pin 501a. (Right lateral expandable body has a bottom guide pin hole that corresponds to top guide pin hole 301b). Such views also show top pin guide hole 302a and the corresponding bottom pin guide hole 303a. Such views also show graft window 311.

Figure 6:
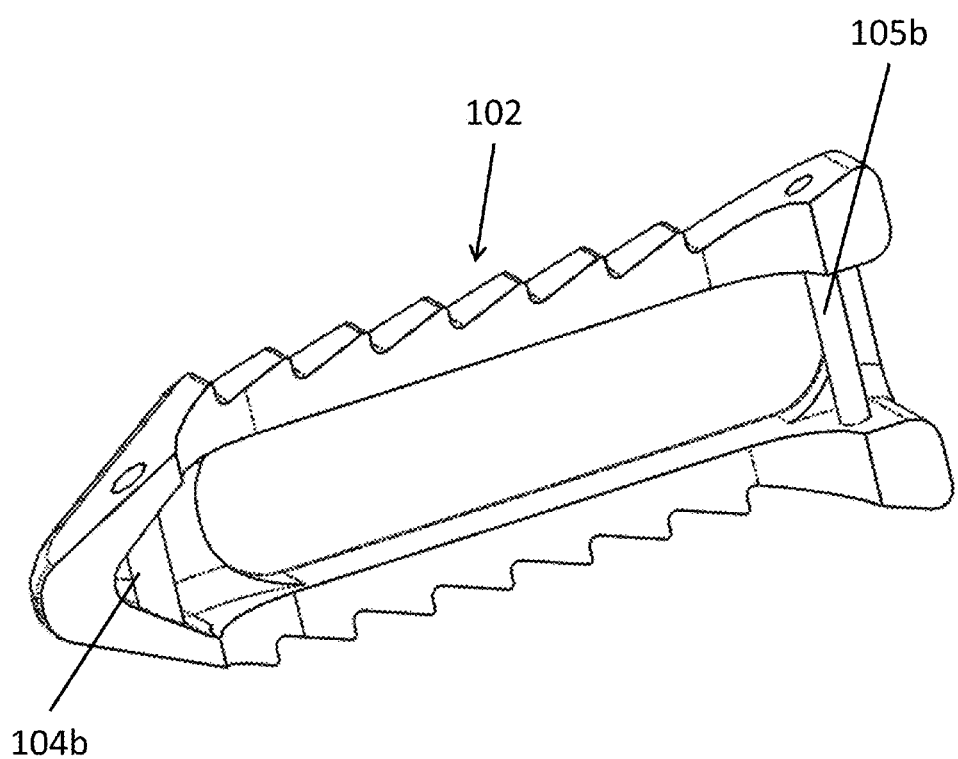
FIG. 6 is a perspective view of the right lateral expandable body of the embodiment of FIG. 1A (with guide pins).
Figure 7:
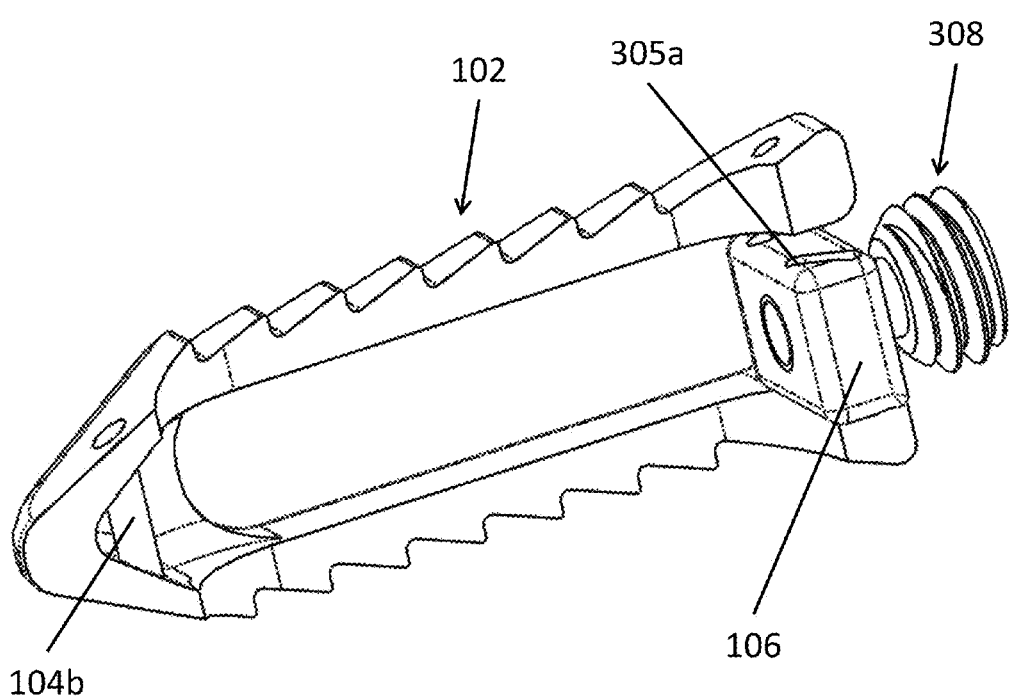
FIG. 7 is a perspective view of the right lateral expandable body of the embodiment of FIG. 1A (with guide pins, translation body, and guide body).

FIG. 6 is a perspective view of the right lateral expandable body 102 of expandable fusion device 100. This view includes guide pins 104b and 105b in place. FIG. 7 is a perspective view of the right lateral expandable body 102 with guide pins 104b and 105b, translation body 202, and guide body 106. Diagonal guide channel 305a (for guide pin 105a) is also shown in guide body 106.

Figure 8A:
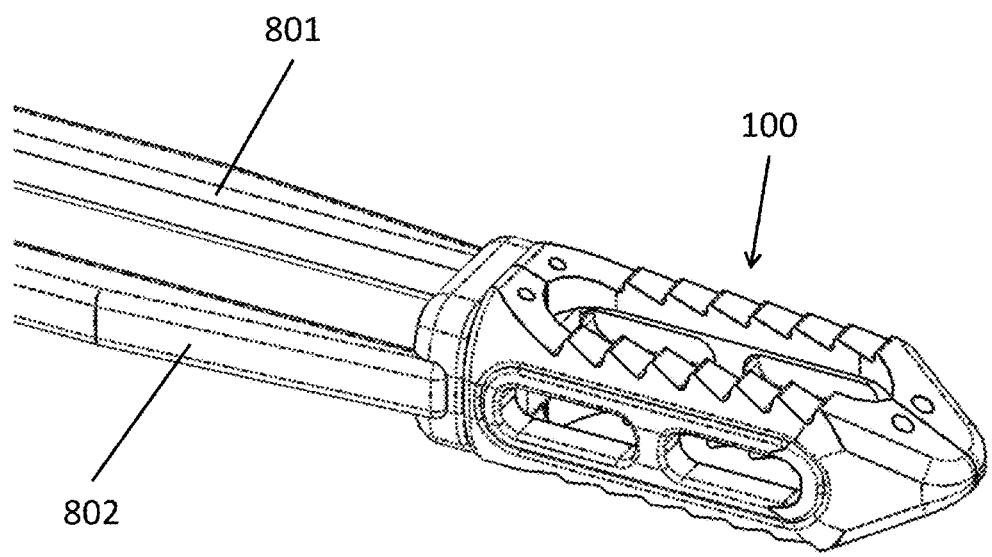
FIG. 8A is a perspective view of the embodiment of FIG. 1A (in the closed position) with the insert device.
Figure 11:
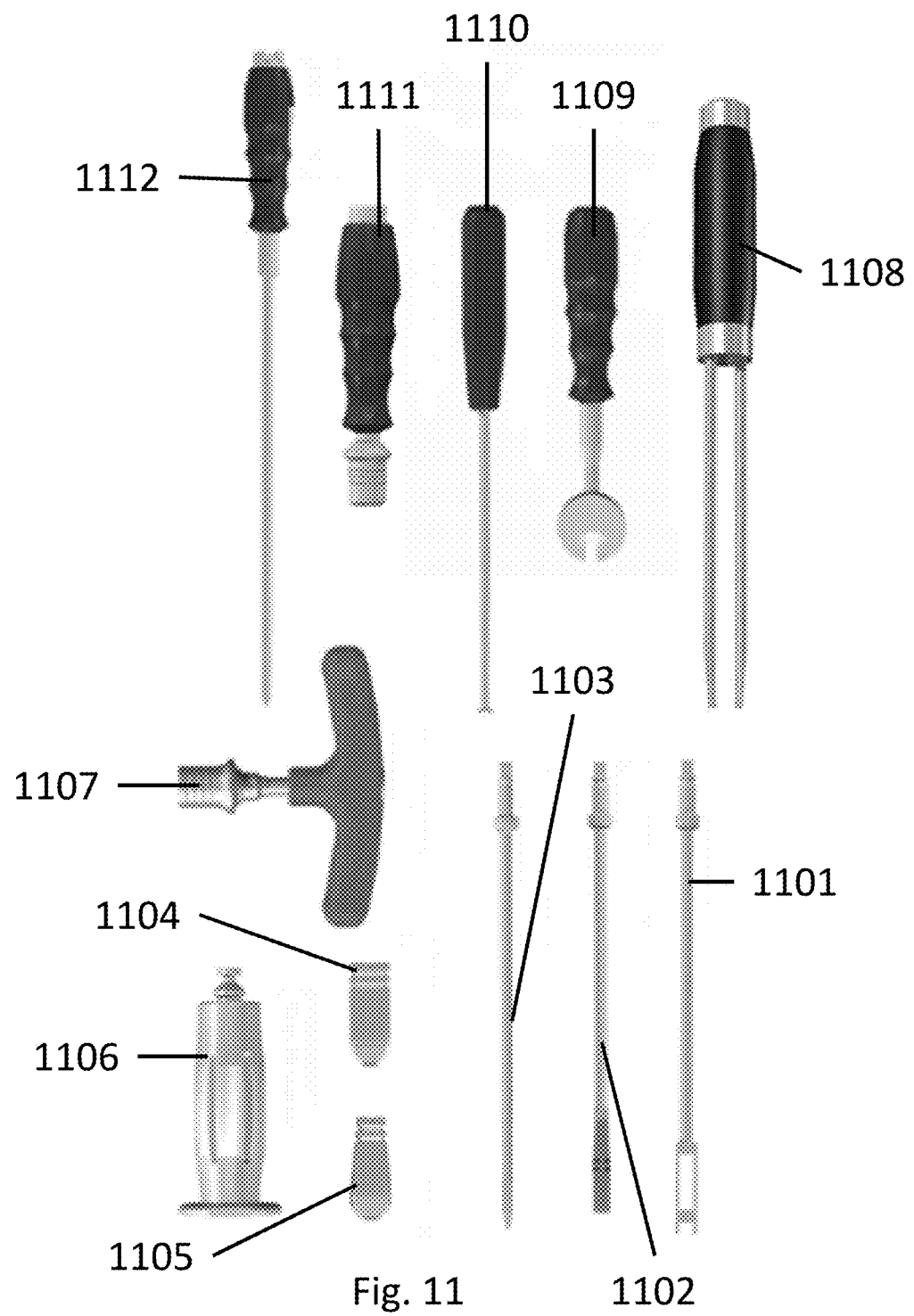
FIG. 11 are illustrations of instruments that can be used in conjunction with the embodiment of FIG. 1A during a surgical technique.

FIG. 8A is a perspective view of expandable fusion device 100 (in the closed position) with inserter 1108 (shown in FIG. 11) having inserter arms 801 and 802. The inerter 1108 is capable of positioning the expandable fusion device 100 in place, and then keeping main body 103 in position (and stationary) as inserter 1108 is also used to couple with translation body 202. This inserter 1108 can then rotate translation body 202, thereby moving guide body 106, which in turn moves left lateral expandable body 101 and right lateral expandable body 102 outward relative to the axis of main body 103.

Figure 8B:
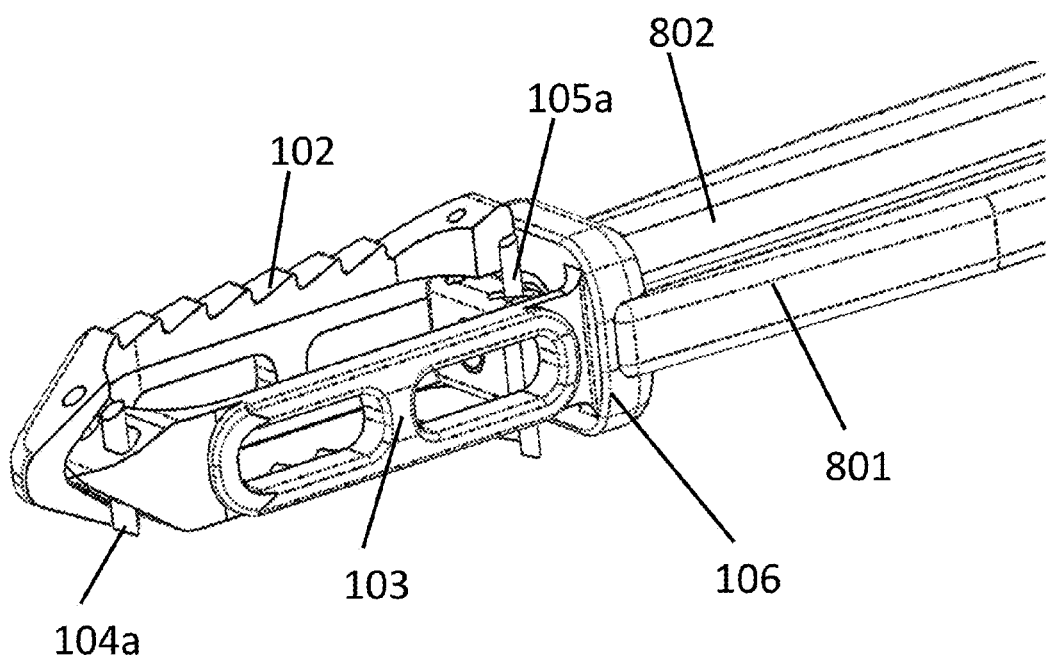
FIG. 8B is a perspective view of the embodiment of FIG. 1A (in the open position) with the insert device (and without the left lateral expanding body).

FIG. 8B is a perspective view of expandable fusion device 100 (in the partially open position) with the inserter arms 801 and 802 (and without the left lateral expanding body 101). As shown guide body 106 has been moved further toward the front of main body 103 which then moves guide pins 105a and 105b within diagonal guide channels 305a and 305b, respectively, which moves these guide pins 105a and 105b outward.

In some embodiments, the inserter 1108 does not include the rotating portion and a separate rotating tool that can couple with translation body 202 can be utilized.

Method of Using Expandable Fusion Device

The expandable fusion devices (such as expandable fusion device 100) can be used for spinal fusion surgery to provide support and structural stability at the fusion site following discectomy. Such expandable fusion devices can be used for spinal fusion, such as spinal fusion procedures in skeletally mature patients with degenerative disc disease (DDD) at one or two contiguous levels of the lumbosacral spine (L2-S1). DDD is defined as back pain of discogenic origin with the degeneration of the disc confirmed by history and radiographic studies. These patients generally should have had six months of non-operative treatment prior to treatment with an intervertebral cage (such as expandable fusion device 100). In addition, these patients may have up to Grade 1 spondylolisthesis or retrolisthesis at the involved levels. An expandable fusion device of the present invention with associated system can be used with supplemental fixation and autograft to facilitate fusion and is implanted via a posterior approach.

The footprint of expandable fusion devices of the present invention has a hollow center to accommodate bone graft. Expandable fusion device 100 is available in various heights to accommodate variability among patients and the inferior and superior surfaces are designed with ridges to improve fixation and stability and prevent back out and migration. The expandable fusion devices can include one or more tantalum markers per ASTM F560 for radiographic visualization.

Figure 9:
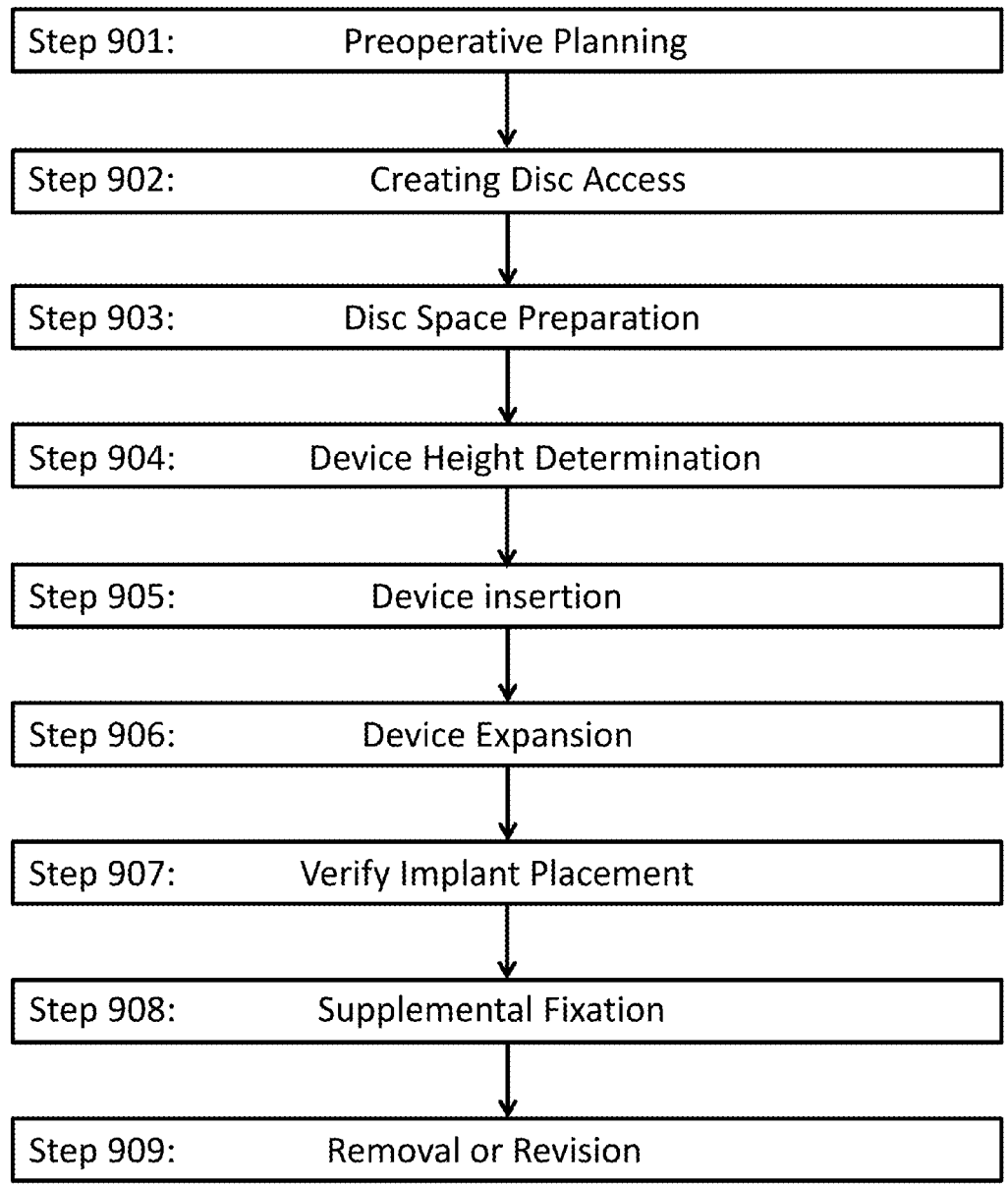
FIG. 9 is a flowchart of a surgical technique using the embodiment of FIG. 1A.

FIG. 9 is a flowchart of a surgical technique using the expandable fusion device 100. FIGS. 10A-10G are illustrations from this surgical technique.

In step 901, the surgeon/practitioner performs preoperative planning. This includes determination of the appropriate height of the expandable fusion device 100 before the surgery. To achieve maximal segment stability, the implant should be selected having the largest possible height that can be safely inserted without disturbing the surrounding neural elements. Typically, the height is between 8 and 14 mm.

Figure 10A:
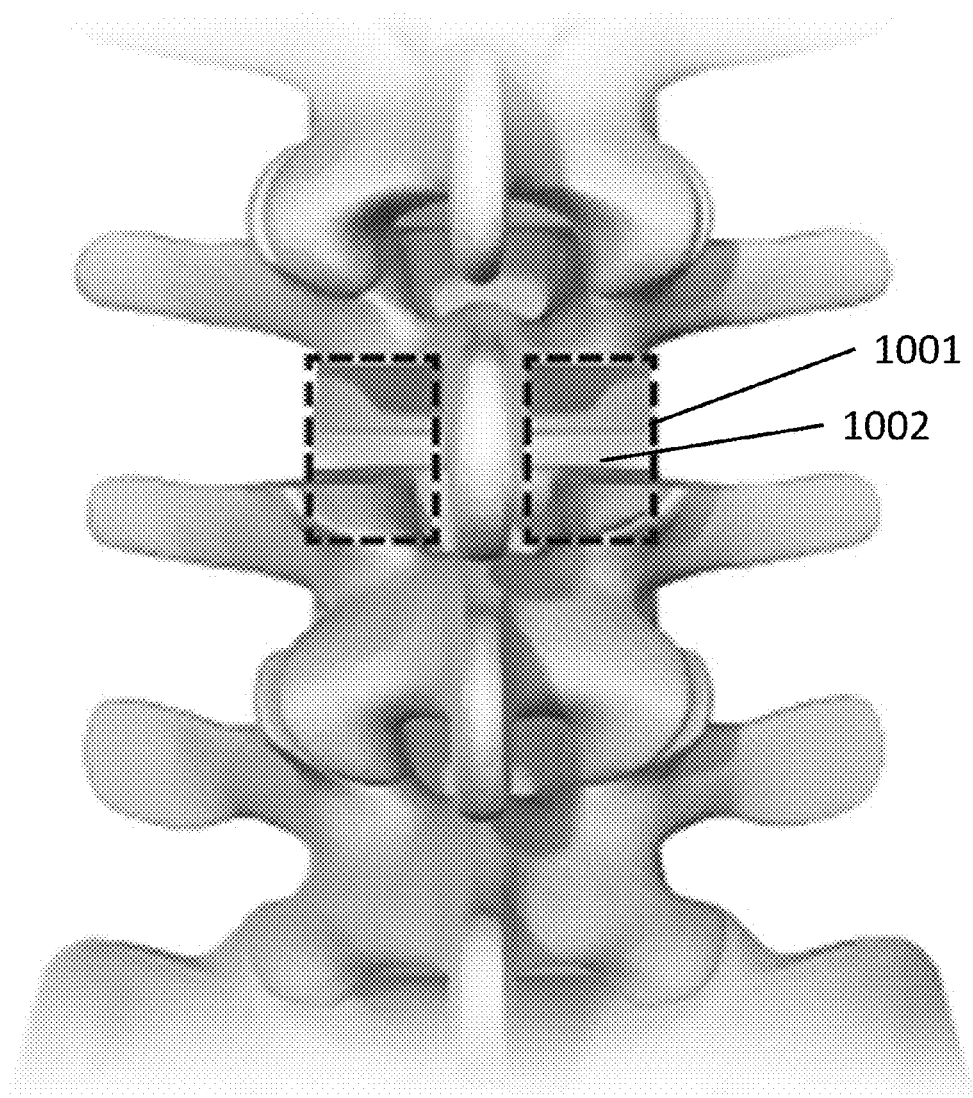
FIGS. 10A-10F are illustrations of from portions of the surgical technique shown in the flowchart of FIG. 9.

In step 902, the surgeon/practitioner creates disc access. For instance, the patient is placed in the prone position. From the midline laterally, the surgeon/practitioner dissect the skin, subcutaneous tissues, and the paraspinal muscles to locate the spinous process, lamina, dura, facets and nerve roots at the appropriate level(s). The surgeon/practitioner performs a laminotomy and carefully retract the dura to expose the disc space. This exposed disc space 1001 and disc 1002 are shown in FIG. 10A.

Figure 10B:
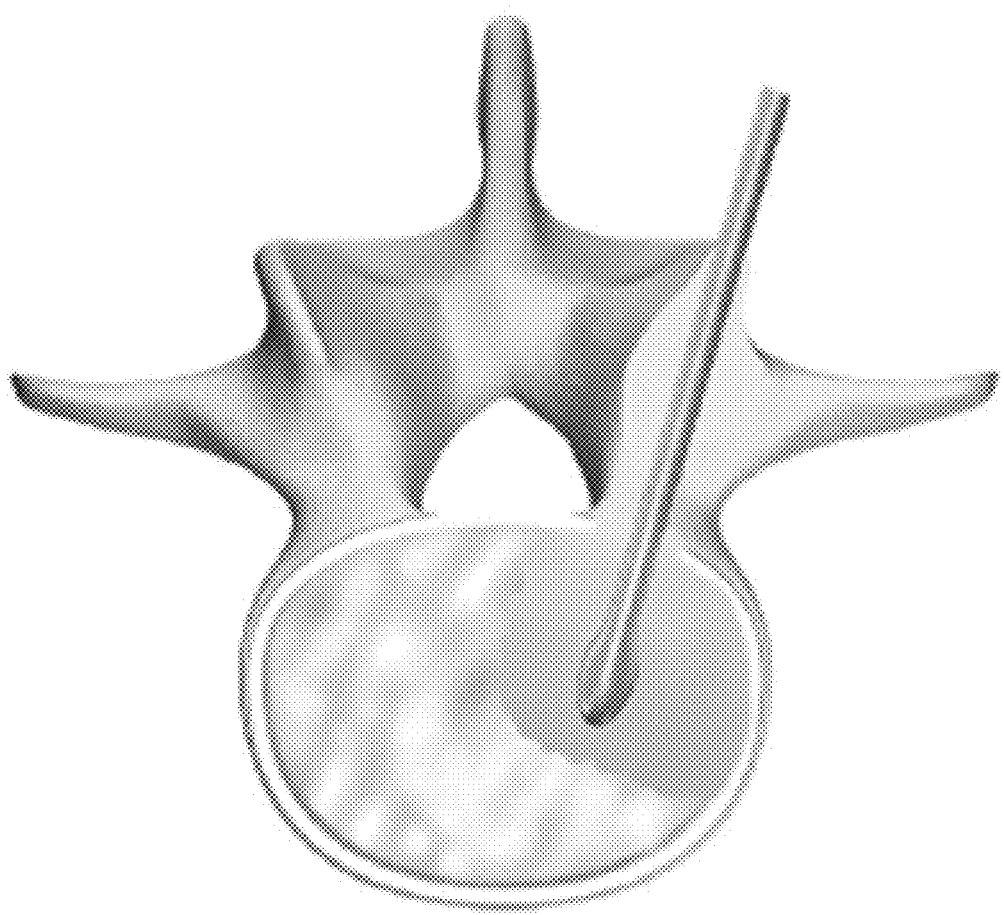

In step 903, the surgeon/practitioner prepares the disc space. Using the appropriate instruments, the surgeon/practitioner remove the disc 1002 material. A box chisel 1101 (shown in FIG. 11) may be used to enlarge the entry and remove posterior osteophytes. The surgeon/practitioner can scrape the cartilaginous layers from the surface of adjacent vertebral endplates until bleeding bone is obtained. Such step is illustrated in FIG. 10B. The surgeon/practitioner should use caution to avoid damage to the endplates.

Figure 10C:
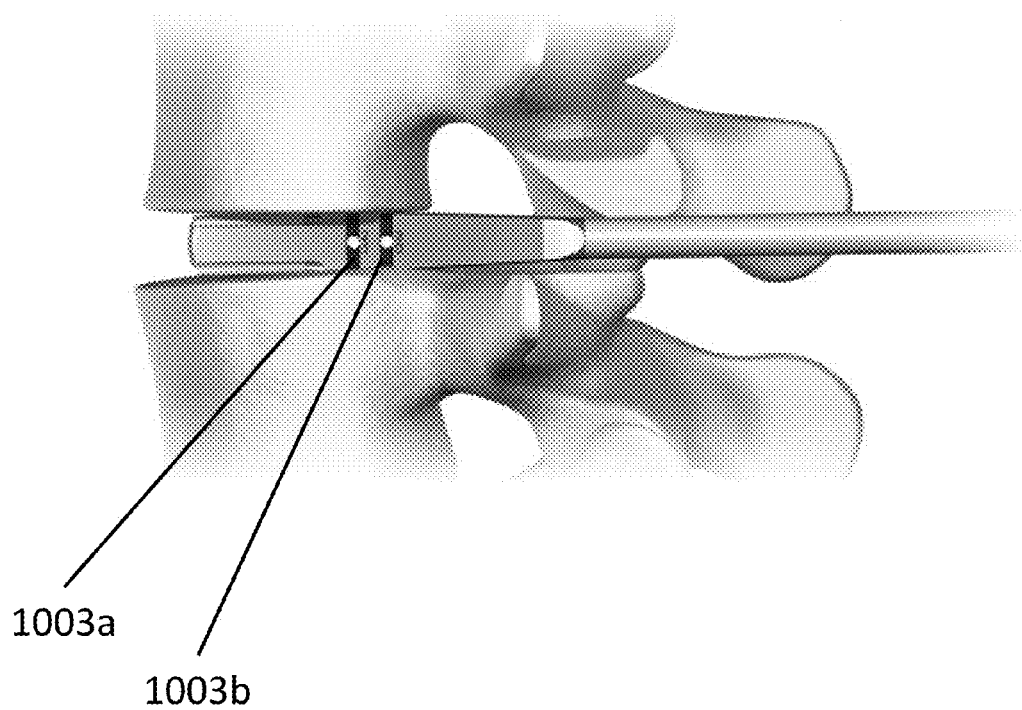

In step 904, the surgeon/practitioner makes a height determination. The surgeon/practitioner can select the paddle shaver 1102 that corresponds to the preoperative estimated height and the prepared endplates. Holes with laser marks for depth indication are typically cut into the paddle shaver at preset distances 1003a and 1003b (such as at 25 mm and 30 mm, respectively). The surgeon/practitioner can insert the paddle shaver 1102 into the disc space and rotate until the desired height is achieved. Such step is illustrated in FIG. 10C. The surgeon/practitioner again should use caution to avoid damage to the endplates. The surgeon can confirm height and position, such as under fluoroscopy.

Figure 10D:
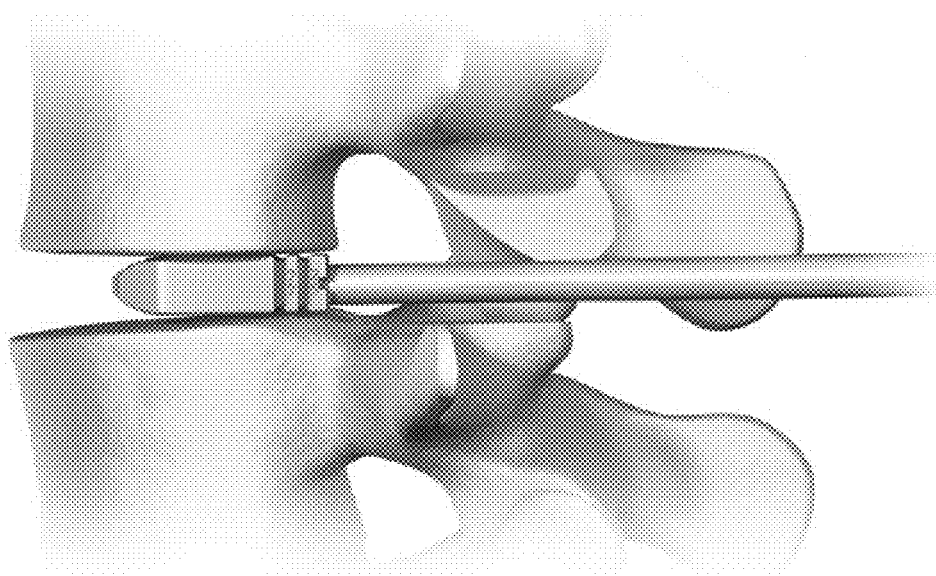

The surgeon/practitioner should then select the trial that corresponds to the preoperative estimated height and paddle shaver 1102 if applicable. Trials that can be selected include parallel trials 1104 and lordotic trials 1105. For instance, a 28 mm trial can have grooves for depth indication at 22 mm and 25 mm. The surgeon/practitioner can attach the trial to the multi-tool 1112 or the inserter 1108 and insert the trial into the disc space. The surgeon/practitioner can apply gentle impaction to ensure that the trial fits tightly and accurately between the endplates. Such step is illustrated in FIG. 10D. The surgeon/practitioner can then confirm height, depth, and position under fluoroscopy. Care must be taken to protect the nerve roots while placing paddle shavers and trials. (This is equally so when inserting the implants, including the expandable fusion device 100).

Figure 10E:
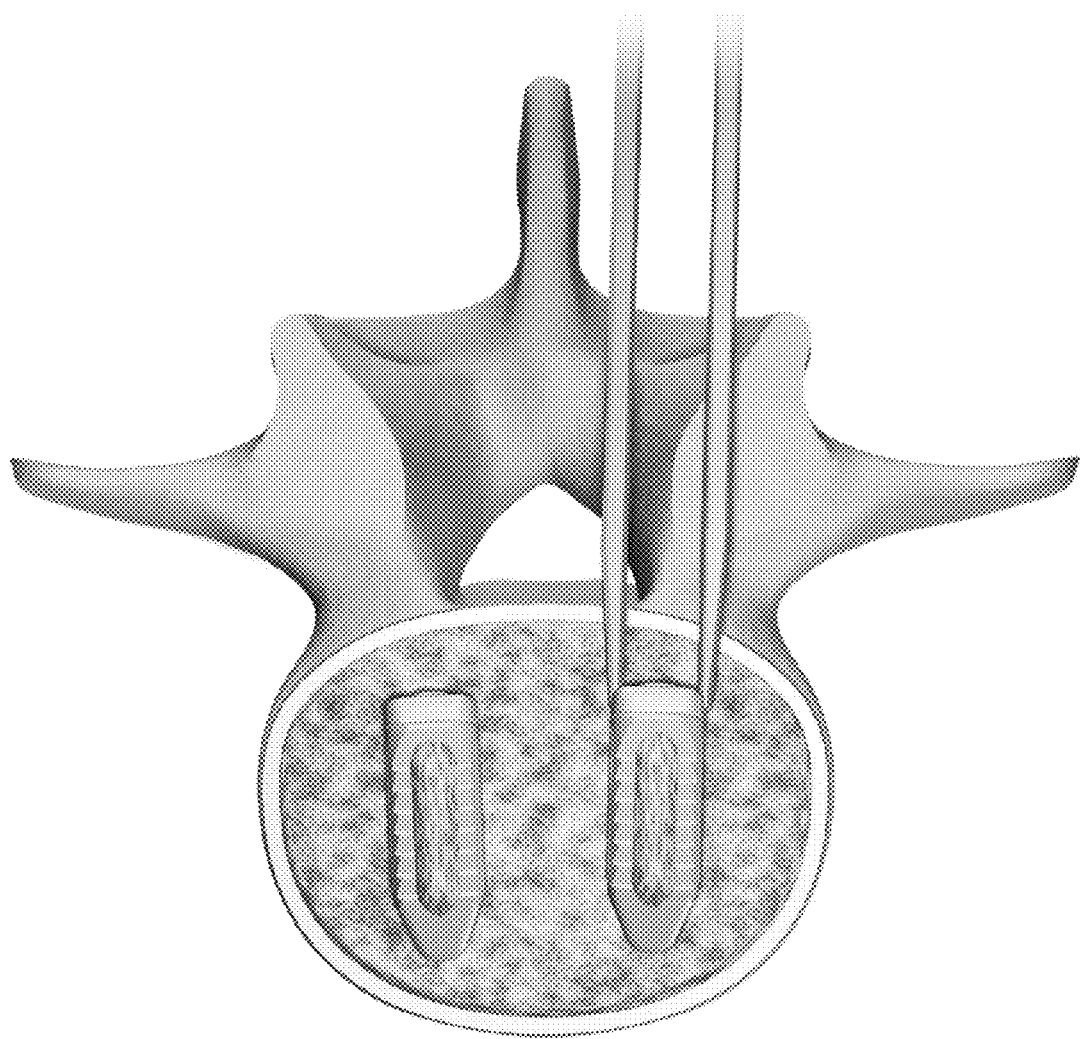

In step 905, the surgeon/practitioner inserts expandable fusion device 100. The surgeon/practitioner selects the expandable fusion device 100 that corresponds to the trial or paddle shaver size. The surgeon/practitioner can attach the expandable fusion device 100 to the inserter 1108 (having insert arms 801 and 802) by aligning the lateral pins with the flat surface of expandable fusion device 100 and turning the handle to expose the internal threaded shaft. The threaded tip of insert 1108 will engage with the central thread of expandable fusion device 100 for secure attachment. The surgeon/practitioner should take care not to over tighten the inserter 1108. The surgeon/practitioner can pack the grafting area of expandable fusion device 100 with bone graft (such as autologous bone graft) in interior space 107 through graft windows 311, 312, and 313, as well as the openings at the top and bottom of expandable fusion device 100. The surgeon/practitioner can insert expandable fusion device 100 into the prepared intervertebral space. Such step is illustrated in FIG. 10E. Gentle impaction on the inserter 1108 will assist in correct positioning.

Figure 10F:
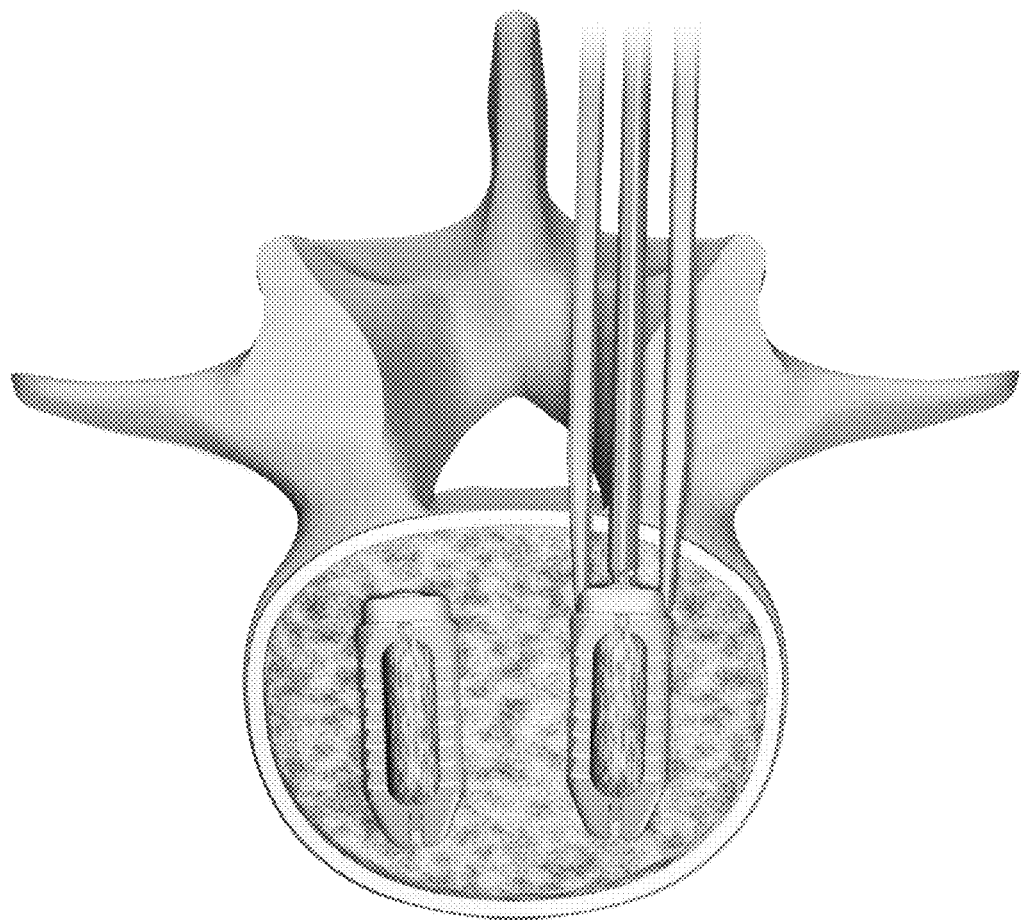

In step 906, the surgeon/practitioner expands expandable fusion device 100. Generally, the inserter 1108 includes a portion that rotating coupler that the surgeon/practitioner can attach to translation body 202. (Alternative, a tool separate from the inserter 1108 can be used to attach to translation body for rotation). The surgeon/practitioner can then rotate translation body 202 to move guide body 106 along the axis of main body 103 of expandable fusion device 100. This movement of guide body 106 opens expandable fusion device 100 by moving left lateral expanding body 101 and right lateral expanding body 102 horizontally outward relative to main body 103. Such step is illustrated in FIG. 10F.

The surgeon/practitioner can then release inserter 1108 from translating body 202. (If this is a separate tool, the surgeon/practitioner can also optionally remove this separate tool at this point in the procedure). Optionally, the surgeon/practitioner can lock the translation body 202 in place using a locking mechanism (not shown). The surgeon/practitioner can then fully release the inserter 1108, such as by turning the handle of inserter 1108 counter-clockwise to disengage from expandable fusion device 100. If additional positioning is required, a tamp may be used with a mallet 1109 to move expandable fusion device 100 to the desired location.

In alternative embodiments, the inserter is attached to the translation body 202 and then either in the same tool or a different tool, arms are then used to keep the device in place and stationary during rotation.

In step 907, the surgeon/practitioner verifies the placement of expandable fusion device 100. Such step is illustrated in FIG. 10F. The surgeon/practitioner can remove inserter 1108 (and any other instruments) and verify the optimal position (such as by using fluoroscopy).

In step 908, the surgeon/practitioner can supplementary fix expandable fusion device 100. For instance an FDA cleared pedicle screw system can be used to fix expandable fusion device 100.

In step 909, and if desired, the surgeon/practitioner can remove or revise expandable fusion device 100. Expandable fusion device 100 can be removed by breaking the fused bone/device interface with a cutting tool (such as an osteotome or chisel). Once expandable fusion device 100 is loose, surgeon/practitioner attach the inserter 1108 and pull expandable fusion device 100 from the disc space. If additional assistance is required, a slap hammer 1106 can be used to retrieve expandable fusion device 100.

A medical procedure kit fully supports the surgical procedure to implant expandable fusion device 100 can be supplied. Such kit can include one or more expandable fusion devices 100 and some or all of the following tools (shown in FIG. 11):

Box chisel 1101.
Paddle shaver 1102.
Paddle starter 1103.
Parallel trial 1104.
Lordotic trial 1105.
Slap hammer 1106.
T-handle 1107.
Inserter 1108.
Mallet 1109.
Impactor 1110.
Handle 1111.
Multi-tool 1112.

The combination of tools and expandable fusion devices 100 can be pre-sterilized for ready use.

The disclosures of all patents, patent applications, and publications cited herein are hereby incorporated herein by reference in their entirety, to the extent that they provide exemplary, procedural, or other details supplementary to those set forth herein. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above.

What is claimed is:

1. An expandable fusion device for being inserted between adjacent vertebrae comprising:
   (a) a main body comprising:
      (i) a main body longitudinal axis that runs from a back end to a tapered front end of the main body,
      (ii) a left side connecting the back end to the tapered front end,
      (iii) a right side connecting the back end to the tapered front end, wherein the main body is of a monolithic construct, and
      (iv) wherein the monolithic main body defines an interior cavity between the back end, the tapered front end, the left side and the front side;
   (b) a left lateral expandable body extending from a back end to a tapered front end, said left lateral expanding body comprising an upper surface, a lower surface and a side surface connecting the upper surface to the lower surface of the left lateral expandable body, wherein each of said upper surface and said lower surface includes teeth projecting therefrom for engaging a corresponding vertebra, and includes a guide pin through hole in the back end and in the tapered front end of the left lateral expandable body, said left lateral expandable body is connected to the main body and configured to move outwardly from the left side of the main body along a latitudinal axis traversing and perpendicular to the main body longitudinal axis while the left lateral expandable body remains parallel to the main body longitudinal axis;
   (c) a right lateral expanding body extending from a back end to a tapered front end, said right lateral expanding body comprising an upper surface, a lower surface and a side surface connecting the upper surface to the lower surface of the right lateral expandable body, wherein each of said upper surface and said lower surface includes teeth projecting therefrom for engaging a corresponding vertebra, and includes a guide in through hole in the back end and in the tapered front end of the right lateral expandable body, said right lateral expandable body is connected to the main body and configured to move outwardly from the right side of the main body along the latitudinal axis while the right lateral expandable body remains parallel to the main body longitudinal axis; and
   (d) a guide body that is operable for moving in the interior cavity within the main body along the main body longitudinal axis, said guide body is movably connected to the main body by a translation body,
      (i) wherein
         (A) the movement of the guide body in a first direction along the main body longitudinal axis moves the left lateral expandable body and the right expandable body outward relative to the main body along the latitudinal axis,
         (B) the movement of the guide body in a second direction, which is opposite to the first direction along the main body longitudinal axis, moves the left lateral expandable body and the right expandable body inward relative to the main body along the latitudinal axis, and
         (C) rotation of the translation body relative to the main body is configured to move the guide body within the main body along the main body longitudinal axis,
      (ii) wherein
         (A) the expandable fusion device has an interior space formed from the main body, left lateral expanding body, and the right lateral expanding body, and
         (B) the interior space is configured to be packed with bone growth inducing substances, and (C) the guide body is operable for the movement using a tool that is not located in whole or in part within the interior space, (iii) wherein
   (A) the left lateral expandable body is movably connected to the main body using a first left guide in and a second left guide pin, and
   (B) the right lateral expandable body is moveable connected to the main body using a first right guide in and a second right guide pin, and (iv) wherein
   (A) the first left guide in and second left guide in are attached to the left lateral expandable body,
   (B) the main body has a left horizontal elongated through channel extending through the tapered front end of the main body and is operable to permit the first left guide in to move within the left horizontal elongated through channel in a horizontal direction that is parallel to the latitudinal axis when attached to the left lateral expandable body, wherein the first left guide in passes through the through holes in the tapered front end of the left lateral expandable body and through the left horizontal elongated through channel in the main body to connect the tapered front end of the main body to the tapered front end of the left lateral expandable body,
   (C) the guide body has a left diagonal through channel operable to permit the second left guide in to move within the left diagonal through channel in a diagonal direction oblique to the main body longitudinal axis when attached to the left lateral expandable body, wherein the second left guide in passes through the through holes in the back end of the left lateral expandable body and through the left diagonal through channel in the guide body to connect the back end of the main body to the back end of the left lateral expandable body, such that the left lateral expandable body moves outward and inward relative to the main body as the guide body moves along the main body longitudinal axis,
   (D) the first right guide in and the second right guide in are attached to the right lateral expandable body,
   (E) the main body has a right horizontal elongated through channel extending through the tapered front end of the main body and is operable to permit the first right guide in to move within the right horizontal elongated through channel in the horizontal direction that is parallel to the latitudinal axis when attached to the right lateral expandable body, wherein the first right guide in passes through the through holes in the tapered front end of the right lateral expandable body and through the right horizontal elongated through channel in the main body to connect the tapered front end of the main body to the tapered front end of the right lateral expandable body,
   (F) the guide body has a right diagonal through channel operable to permit the second right guide in to move within the right diagonal through channel in a diagonal direction oblique to the main body longitudinal axis of the main body when connected to the right lateral expandable body, wherein the second right guide in passes through the through holes in the back end of the right lateral expandable body and through the right diagonal through channel in the guide body to connect the back end of the main body to the back end of the right lateral expandable body, such that the right lateral expandable body moves outward and inward relative to the main body as the guide body is moved along the main body longitudinal axis, and
   (G) the expandable fusion device has a fixed length measured along the main body longitudinal axis, a fixed height measured from the lower surfaces to the upper surfaces of the left lateral expanding body and the right lateral expanding body, and a variable width measured between the side surfaces of the left lateral expanding body and the right lateral expanding body.

2. The expandable fusion device of claim 1, wherein the expandable fusion device is capable of expanding and contracting without changing the fixed height of the expandable fusion device.

3. The expandable fusion device of claim 1, wherein the interior space of the expandable fusion device is unreduced as the guide body is moved in the first direction.

4. The expandable fusion device of claim 1, wherein the variable width can be increased between 1 mm and 6 mm as the guide body is moved in the first direction.

5. The expandable fusion device of claim 1, wherein the variable width can be increased between 10% and 60% as the guide body is moved in the first direction.

6. The expandable fusion device of claim 1, wherein the fixed length is between 22 mm and 28 mm.

7. The expandable fusion device of claim 1, wherein the fixed height is between 8 mm and 14 mm.

8. The expandable fusion device of claim 1, wherein
   (a) the rotation of the translation body in one rotational direction is capable of moving the guide body in the first direction, and
   (b) the rotation of the translation body in an opposition rotational direction that is opposite the one rotational direction is capable of moving the guide body in the second direction.

* * * * *